US008622931B2

(12) United States Patent
Teague et al.

(10) Patent No.: US 8,622,931 B2
(45) Date of Patent: Jan. 7, 2014

(54) EXTRUDED GUIDEWIRES AND METHODS OF MAKING

(75) Inventors: James A. Teague, Spencer, IN (US); Mark A. Voss, Spencer, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1087 days.

(21) Appl. No.: 11/892,805

(22) Filed: Aug. 27, 2007

(65) Prior Publication Data
US 2008/0194991 A1    Aug. 14, 2008

Related U.S. Application Data

(60) Provisional application No. 60/900,360, filed on Feb. 9, 2007.

(51) Int. Cl.
*A61M 25/09*    (2006.01)
(52) U.S. Cl.
CPC ................................. *A61M 25/09* (2013.01)
USPC ........................................................ 600/585
(58) Field of Classification Search
USPC ........................................................ 600/585
See application file for complete search history.

(56) References Cited

U.S. PATENT DOCUMENTS

| | | | | |
|---|---|---|---|---|
| 5,069,226 A | * | 12/1991 | Yamauchi et al. | 600/585 |
| 5,333,620 A | * | 8/1994 | Moutafis et al. | 600/585 |
| 5,674,106 A | | 10/1997 | Cheetham | |
| 6,007,478 A | * | 12/1999 | Siess et al. | 600/16 |
| 6,019,737 A | * | 2/2000 | Murata | 600/585 |
| 6,329,069 B1 | * | 12/2001 | Azizi et al. | 428/600 |
| 6,340,441 B1 | * | 1/2002 | Meyer et al. | 264/173.12 |
| 6,371,929 B1 | | 4/2002 | Steele | |
| 6,464,651 B1 | * | 10/2002 | Hiejima et al. | 600/585 |
| 7,011,636 B2 | * | 3/2006 | Tenerz | 600/585 |
| 7,074,197 B2 | | 7/2006 | Reynolds et al. | |
| 2003/0032897 A1 | * | 2/2003 | Burmeister et al. | 600/585 |
| 2003/0229298 A1 | * | 12/2003 | Iwami et al. | 600/585 |
| 2004/0106878 A1 | * | 6/2004 | Skujins et al. | 600/585 |
| 2004/0167439 A1 | * | 8/2004 | Sharrow | 600/585 |
| 2005/0054953 A1 | * | 3/2005 | Ryan et al. | 600/585 |
| 2005/0080448 A1 | * | 4/2005 | Kear et al. | 606/200 |
| 2005/0124917 A1 | * | 6/2005 | Skujins et al. | 600/585 |
| 2007/0299366 A1 | * | 12/2007 | Sharrow et al. | 600/585 |
| 2008/0154152 A1 | * | 6/2008 | Satou et al. | 600/585 |

FOREIGN PATENT DOCUMENTS

| | | |
|---|---|---|
| WO | WO 97/32625 | 9/1997 |
| WO | WO 99/46109 | 9/1999 |
| WO | WO 03/099371 A1 | 12/2003 |
| WO | WO 2005/120598 A1 | 12/2005 |

OTHER PUBLICATIONS

Written Opinion and International Search Report for PCT/US2007/078164.

* cited by examiner

*Primary Examiner* — Sean Dougherty
*Assistant Examiner* — Michael C Stout
(74) *Attorney, Agent, or Firm* — Bookoff McAndrews, PLLC

(57) ABSTRACT

Embodiments of the invention include a guidewire for use in a medical procedure. Embodiments of the invention may include a guidewire having an elongate core wire where the core wire is unground, has a length, and a substantially uniform cross-section. A thermoplastic material is extruded with the core wire and surrounds a portion of the core wire. Another embodiment is directed to a method of manufacturing a guidewire including providing an unground core wire having a length, providing a thermoplastic material, and extruding the thermoplastic material onto the core wire such that a portion of the wire is surrounded by the thermoplastic material.

16 Claims, 4 Drawing Sheets

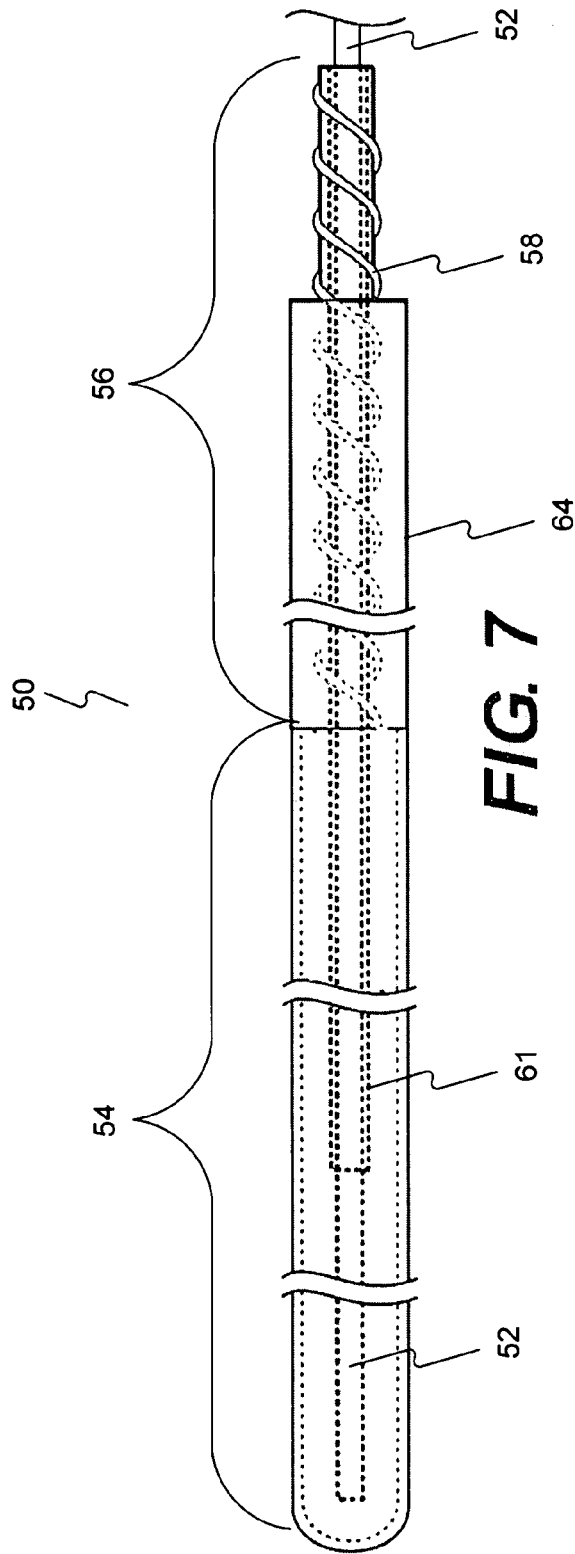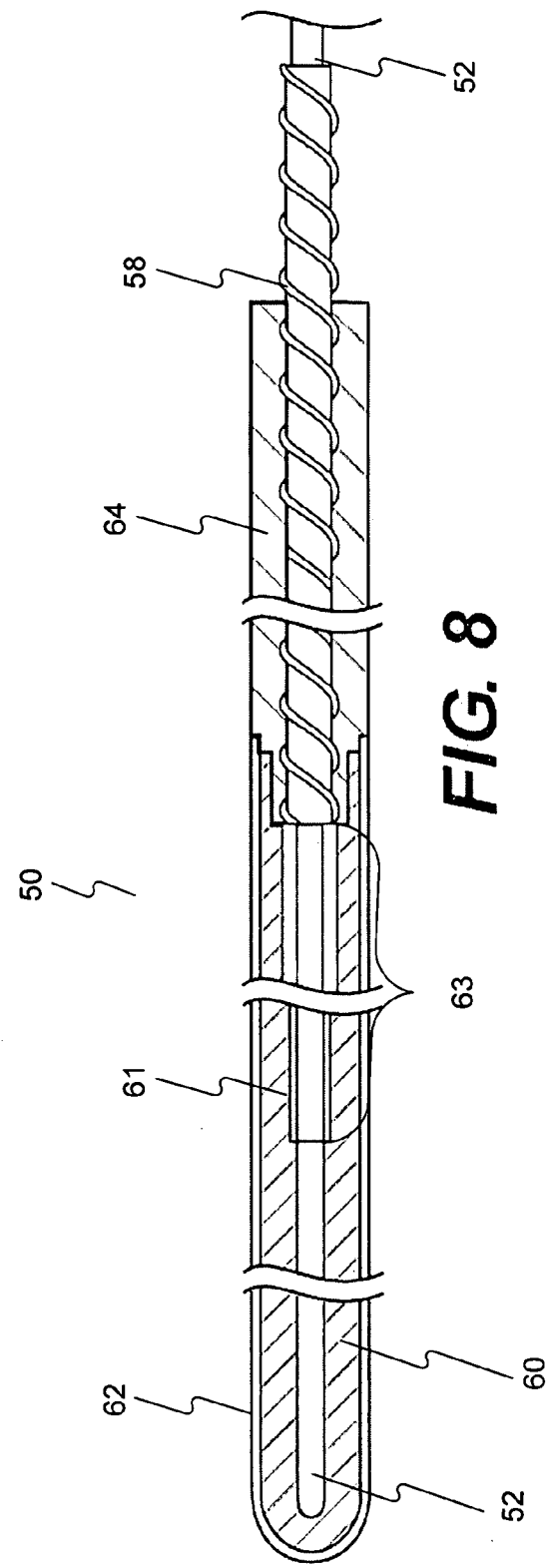

EXTRUDED GUIDEWIRES AND METHODS OF MAKING

CROSS REFERENCE TO RELATED APPLICATIONS

This application claims the benefit of U.S. Provisional Application No. 60/900,360, filed Feb. 9, 2007, under 35 U.S.C. §119(e). The entire disclosure of that provisional application is incorporated by reference herein.

FIELD OF THE INVENTION

The present invention generally relates to guidewires and their methods of manufacture. Specifically, the present invention relates to guidewires for use in medical applications, including urological applications. Those skilled in the art will recognize the benefits of applying the present invention to similar fields not discussed herein.

BACKGROUND OF THE INVENTION

Guidewires are used in a variety of medical applications including intravascular, gastrointestinal, and urological. For example, a common vascular application is Percutaneous Transluminal Coronary Angioplasty (PTCA). This procedure can involve inserting a guidewire through an incision in the femoral artery near the groin, advancing the guidewire over the aortic arch, into a coronary artery, and across a lesion to be treated in the heart. Similarly, angioplasty performed in other parts of the anatomy is called Percutaneous Transluminal Angioplasty (PTA) and may also involve the use of a guidewire. Typical vascular guidewires are about 50 cm to 300 cm in length, and are about 0.010-0.038 inches in diameter depending upon the application.

Common gastrointestinal uses of guidewires include endoscopic procedures in which an endoscope may be inserted into the mouth and advanced through the esophagus to the bile duct, the cystic duct, or the pancreatic duct. A guidewire is then threaded through a lumen in the endoscope and into the bile duct, cystic duct, or pancreatic duct. For purposes of this disclosure, "distal" refers to the end further from the device operator during use and "proximal" refers to the end closer to the device operator during use. Once the distal tip of the guidewire is located in a position desired to be treated, a diagnostic or therapeutic medical instrument is advanced over the guidewire and to the treatment area. The guidewire and the instrument may then be observed through the endoscope as treatment occurs.

Urological uses of guidewires include the placement of ureteral stents, or the placement of a basket-type retrieval device to retrieve kidney stones. Ureteral stenting, for example, is required when the normal flow of urine from the kidney into the bladder is compromised perhaps by tumor growth, stricture, or stones. Generally, the procedure involves the insertion of a ureteroscope through the urethra and into the bladder. A guidewire is then advanced through the ureteroscope and into a ureter. The wire is then forced through the compromised portion of the ureter. Once the guide wire is in place, a ureteral stent is advanced over the guidewire and into position in the ureter. The guidewire may then be removed and the stent will maintain the patency of the fluid path between the kidney and the bladder. The procedures described above are but a few of the known uses for guidewires.

Pushability, kink resistance, torqueability, and bendability are closely related and important features of a guidewire. It is important that force applied at the proximal end of a guidewire is transferred to the distal end of the guidewire. In addition, a guidewire must exhibit good bendability. This characteristic is a balance between adequate flexibility to navigate a tortuous lumen and suitable rigidity to support tracking of another device such as a catheter. Torqueability is closely related to the torsional rigidity of the wire and is ultimately demonstrated by how well rotation imparted to the proximal end of the guidewire is translated to the distal end of the guidewire.

Kink resistance is also an important characteristic of a guidewire. Kink resistance is closely related to the stiffness of the wire. Very stiff wires often provide good pushability (axial rigidity) but poor kink resistance. Kink resistance is measured by the ability of the guidewire to be forced into a relatively tight bend radius without permanently deforming the wire. A kink can lead to an improper force transfer and pushability along the guide wire.

Many guidewires exhibit a transition in stiffness along their length from a relatively more stiff portion in the proximal end to a relatively less stiff portion in the distal end. This provides a more desirable combination of pushability and the ability to navigate tortuous vessels. For some applications, the preferred transition is a smooth and continuous transition from stiffer to less stiff.

Several different types of guidewires are well known in the art. One type of known wire is characterized by a solid metal core surrounded by a metal coil. Typical metals for the core may include spring steels and stainless steels. Coils are usually made of the same variety of metals used as core materials. The coil is usually made of round wire or flat wire and surrounds either the entire length of the core or only a portion of the core. The coil usually is formed by helically wrapping the wire around a mandrel, removing the mandrel, and inserting the core into the coil. The pitch of the wire coil may be varied along the length of the coil to vary the stiffness of the coil. Changes in the pitch of the coil can result in flexibility changes to the resulting guidewire structure.

Traditional coil over core wires also achieve a transition in stiffness along their length by using a ground core. In current guidewire technology, for example, the distal tip of the core is usually ground to a taper to provide the characteristics of added flexibility near the tip. In the above described examples, the core wire portion of the guidewire is formed from a base cylindrical metal stock material that is then machined down to a predetermined profile and cross-sectional configuration.

The stock material used for guidewire construction is usually a continuous length of cylindrical wire cut to a desired length after machining. The cylindrical stock material is machined along certain portions to obtain a desired outer diameter to control flexibility. The grinding required to alter the device's flexibility is usually accomplished with a particular manufacturing machine tool called a center-less grinder. Often using a rotating cutting wheel/blade, a centerless grinder cuts away portions of the stock material profile to attain a precise desired configuration. For example, a known centerless grinder machine tool is described in U.S. Pat. No. 5,674,106, the entire contents of which are hereby incorporated by reference.

The use of a center-less grinder machine has a number of undesirable drawbacks related to the manufacture of guidewires. For example, the operation of a center-less grinding machine is a labor intensive procedure that requires an experienced operator. In addition, the process results in a relatively high scrap rate, resulting in excess material cost. Moreover, center-less grinding stations, including the actual machinery and related components, leave a large footprint occupying valuable and costly production space otherwise available for alternative uses. Despite these drawbacks, and since guidewire flexibility is largely determined based on the resulting machined profile of the base core wire, dependable alternative configurations and methods of manufacture have, as of yet, not been successful.

The profile and cross-sectional configurations of guidewires formed with a center-less grinding machine inherently results in distinct portions having a smooth or tapered cylindrical outer diameter. The inherent cylindrical configuration results in a number of characteristics that hinder the desired performance of such guidewires during use. For example, the outer diameter of the guidewire, even with a fluoropolymer coating, can result in undesired friction during movement within a working channel of an endoscope. The friction results from contact between a relatively large portion of the exterior perimeter of the guidewire against an internal surface of a working channel in an endoscope.

In addition, the inherent cylindrical geometry resulting from center-less grinding also occupies valuable area within the working channel of an endoscope. For example, the necessary area occupied by the inherent geometry of such guidewires limits potential for increased fluid flow within a working channel during irrigation and suction. In addition, the shape of such guidewires can reduce the capability for alternate device passage resulting from potentially unoccupied additional working channel space available with alternative guidewire geometries.

Accordingly, there is a need for alternative guidewire configurations and methods of manufacture that result in guidewires exhibiting the features of pushability, kink resistance, torqueability, and bendability.

SUMMARY OF THE INVENTION

Embodiments of the present invention are directed to guidewires and methods of making that obviate one or more of the limitations and disadvantages of prior guidewires. In one embodiment, a guidewire comprises an elongate core wire. The core wire is unground and has a length and has a substantially uniform cross-section along the length. A thermoplastic material is extruded along the core wire and surrounds a portion of the core wire.

In various embodiments, the guidewire may include one or more of the following additional features: wherein the thermoplastic material covers only a proximal portion of the core wire; wherein the proximal portion of the core wire covered with the thermoplastic material is further covered with a polymer; wherein a portion of the core wire not covered with the thermoplastic material is covered with a polymer; wherein the guidewire is provided without a wire coil surrounding any portion of the core wire; wherein a distal portion of the thermoplastic material is tapered to have a smaller cross-section than a remaining proximal portion of the thermoplastic material; wherein a distal portion of the guidewire is more flexible than a proximal portion of the guidewire that includes the thermoplastic material; wherein the thermoplastic material exhibits a substantially star shaped cross-section; wherein an exterior surface of the thermoplastic material comprises a plurality of fins; wherein each of the plurality of fins is separated along the exterior surface of the thermoplastic material by one of a plurality of troughs; wherein a non-tapered portion of the thermoplastic material has an exterior surface comprising a plurality of fins; wherein each of the plurality of fins is separated along the exterior surface of the thermoplastic material by one of a plurality of troughs; wherein the thermoplastic material comprises silicone, vinyl, polyethylene, polypropylene, nylon, acrylic, styrene, polycarbonate, polyether block amide, fluoropolymer, or combinations thereof; and wherein the core wire comprises stainless steel, titanium, metallic alloys of nickel/titanium, copper, cobalt, vanadium, chromium, iron, or combinations thereof.

Another embodiment is directed to a guidewire comprising an elongate core wire. The core wire is unground, has a length and has a substantially uniform cross-section along the length. In addition, a wire coil wrapped around a proximal portion of the core wire.

In various embodiments, the guidewire may include one or more of the following additional features: wherein the proximal portion of the core wire having the wire coil thereon is covered with a polymer; wherein a distal portion of the core wire not wrapped with the wire coil is covered with a polymer; wherein the wire coil is wrapped around the core wire such that a proximal portion of the guidewire has a larger cross-section than a distal portion of the guidewire; and wherein the wire coil is wrapped around the core wire such that a proximal portion of the guidewire is less flexible than a distal portion of the guidewire.

Another embodiment is directed to a method of manufacturing a guidewire. The method comprises providing an unground core wire having a length, providing a thermoplastic material, and extruding the thermoplastic material onto the core wire such that a portion of the wire is surrounded by the thermoplastic material.

In various embodiments, the method may include one or more of the following additional features: wherein providing the core wire includes extruding the core wire along with the thermoplastic material; wherein manufacturing the guidewire does not include providing a coil wire surrounding any portion of the core wire; wherein the core wire has a substantially uniform cross-section along the length; wherein the thermoplastic material is extruded to cover only a proximal portion of the core wire; further comprising covering the proximal portion of the core wire covered with the thermoplastic material with a polymer; wherein the polymer is applied by a heat shrinking process; further comprising covering a portion of the core wire not covered with the thermoplastic material with a polymer; further comprising tapering a distal portion of the thermoplastic material to increase the flexibility of a distal portion of the guidewire; wherein the thermoplastic material comprises silicone, vinyl, polyethylene, polypropylene, nylon, acrylic, styrene, polycarbonate, polyether block amide, fluoropolymer, or combinations thereof; wherein the core wire comprises stainless steel, titanium, metallic alloys of nickel/titanium, copper, cobalt, vanadium, chromium, iron, or combinations thereof; wherein the extruded thermoplastic material exhibits a substantially star shaped cross-section; wherein the extruded thermoplastic material has an exterior surface comprising a plurality of fins; wherein each of the plurality of fins is separated along the exterior surface of the thermoplastic material by one of a plurality of troughs; and wherein a non-tapered portion of the thermoplastic material is provided with an exterior surface comprising a plurality of fins.

Another embodiment is directed to a method of manufacturing a guidewire. The method comprises providing an unground core wire having a length and a substantially uniform cross-section along the length, providing wire coil; and wrapping a wire coil around a proximal portion of the core wire.

In various embodiments, the method may include one or more of the following additional features: further comprising covering the proximal portion of the core wire having the wire coil thereon with a polymer; wherein the polymer is applied by a heat shrinking process; further comprising covering the distal portion of the core wire not wrapped with the wire coil with a polymer; wherein wrapping the wire coil around the core wire forms a proximal portion of the guidewire having a larger cross-section than a distal portion of the guidewire; and wherein wrapping the wire coil around the core wire forms a proximal portion of the guidewire that is less flexible than a distal portion of the guidewire.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 7 is a side view of a portion of a guidewire, according to another embodiment of the invention.

FIG. 8 is a cross-sectional view of the guidewire of FIG. 7 taken along line 8-8 in FIG. 7.

DESCRIPTION OF THE EMBODIMENTS

Figure 1:
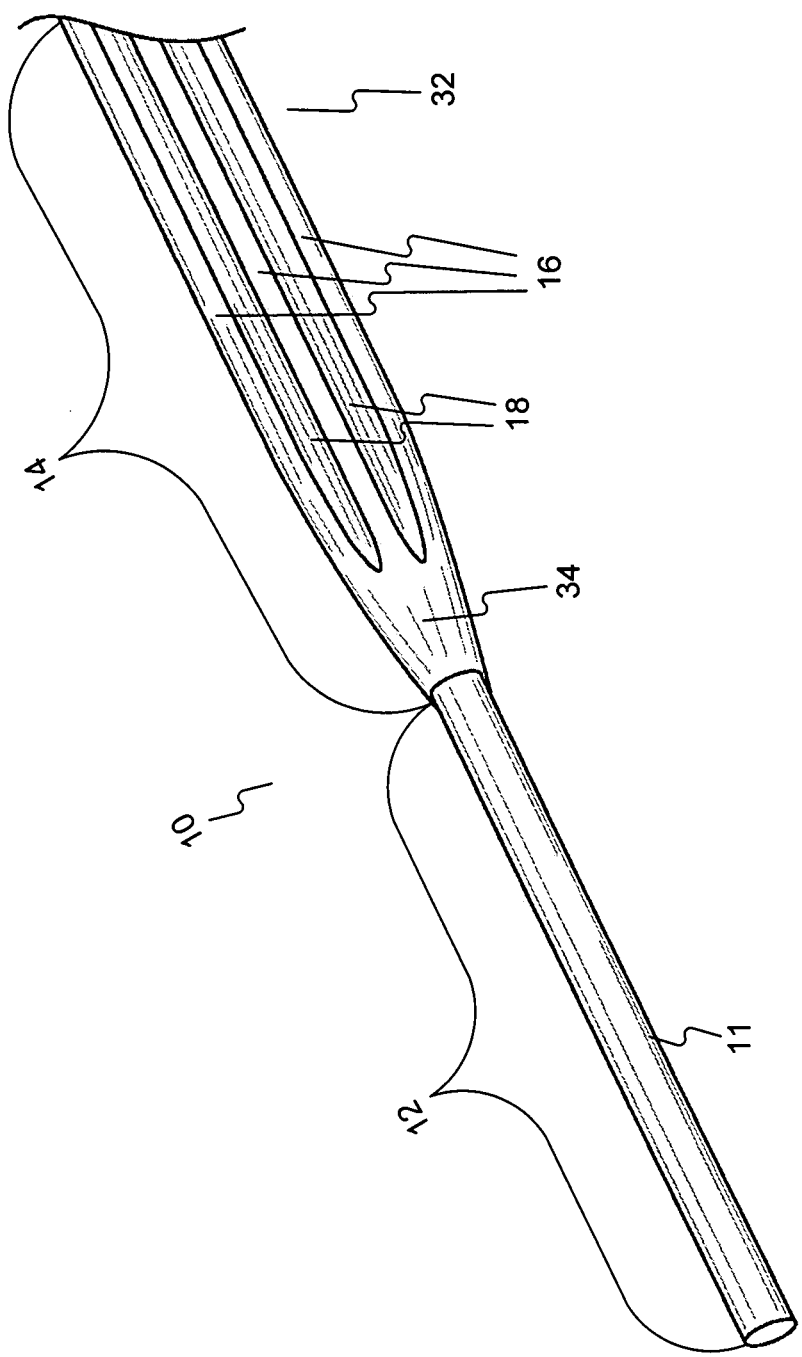
FIG. 1 is a perspective view of an extruded core for a guidewire, according to one embodiment of the invention.

Reference will now be made in detail to the present exemplary embodiments of the invention, examples of which are illustrated in the accompanying drawings. Wherever possible, the same reference numbers will be used throughout the drawings to refer to the same or like parts. The drawing figures of this application are intended to provide a general understanding of the working elements of the underlying system. Accordingly, unless explicitly stated, the figures do not represent a literal depiction of proportional dimensions or the precise locations for the illustrated inter-related components. In addition, for purposes of this application, an "unground" material includes a material having an exterior surface not further machined (e.g., ground in a centerless grinder, milled, or lathed) from its initial configuration.

FIG. 1 illustrates a perspective view of a distal portion of a core wire for a guidewire, according to one embodiment of the invention. FIG. 1 depicts a core wire assembly 10 having a distal portion 12 and a proximal portion 14. An underlying core wire 11 is provided as a base component of the core wire assembly 10. As will be described in more detail below, the core wire 11 of the core wire assembly 10 can be combined with a co-extruded thermoplastic or multiple thermoplastics. The use of thermoplastics combined with an underlying base wire (e.g., either a machined or an "unground" wire) to form a core wire assembly 10 allows for control over the resulting flexibility of the device by the selection of thermoplastics with a wide range of durometers.

As seen in FIG. 1, the co-extruded thermoplastic material(s) is/are depicted generally by reference number 32. Additionally, in additional embodiments, items 28 and 29 of FIG. 3 and items 62 and 60 of FIG. 8 represent co-extruded materials. Exemplary thermoplastic materials include, but are not limited to, silicone, vinyl, polyethylene, polypropylene, nylon, acrylic, styrene, polycarbonate, polyether block amide, thermoplastics sold under the trademark PEEK (including a repeat unit that comprises of oxy-1,4-phenylenoeoxy-1,4-phenylene-carbonyl-1,4-phenylene), and fluoropolymers (such as PTFE (polytetrafluoroethylene)). The potential for a selection of a wide range of materials, with different durometers, allows for variation and control of the resulting guidewire characteristics of pushability, kink resistance, torqueability, and flexibility. In addition, precise control over the resulting material characteristics can produce a guidewire device not requiring an external wrapped coil or the use of a center-less grinder.

A distal portion of the core wire 11 is not covered with material 32 and therefore exhibits a smaller cross-sectional profile as compared to the proximal portion 14. Accordingly, as seen in FIG. 1, the distal portion 12 may exhibit a smaller diameter circular cross-section, while the proximal portion exhibits a larger cross-sectional profile. In addition, the material 32 can be provided such that the profile of the proximal portion 14 tapers down to the smaller diameter of the distal portion 12 along a tapered portion 34 at the distal end of the proximal portion 14. As described in more detail below, the core wire assembly 10 can be further manufactured to include polymeric coatings, such as, for example, polytetrafluoroethylene or polyethylene heat shrunk over the distal and proximal portions, thereby forming a completed guidewire.

As will be described in more detail below, material 32 along the proximal portion 14 can be formed to have a grooved configuration comprised of fins 16 extending between troughs 18 along the outside surface of the proximal portion 14. The troughs 18 along the outside surface of the proximal portion 14 reduce the amount of exterior surface area available for contact against an internal surface of a working channel in an endoscope during use. Accordingly, as a result of this configuration, friction hindering relative movement between a guidewire having a core wire assembly 10 and an internal working channel of an endoscope is reduced. Moreover, such a grooved configuration results in increased fluid flow within a working channel by means of the increased area available within the working channel lumen by means of the troughs 18. As will be described in detail below, a guidewire using a core wire assembly 10 exhibits the required characteristics of pushability, kink resistance, torqueability, and flexibility without requiring the use of a core wire formed with a centerless grinding machine and without requiring the inclusion of a wire coil wrapped around the core wire assembly 10.

Figure 2:
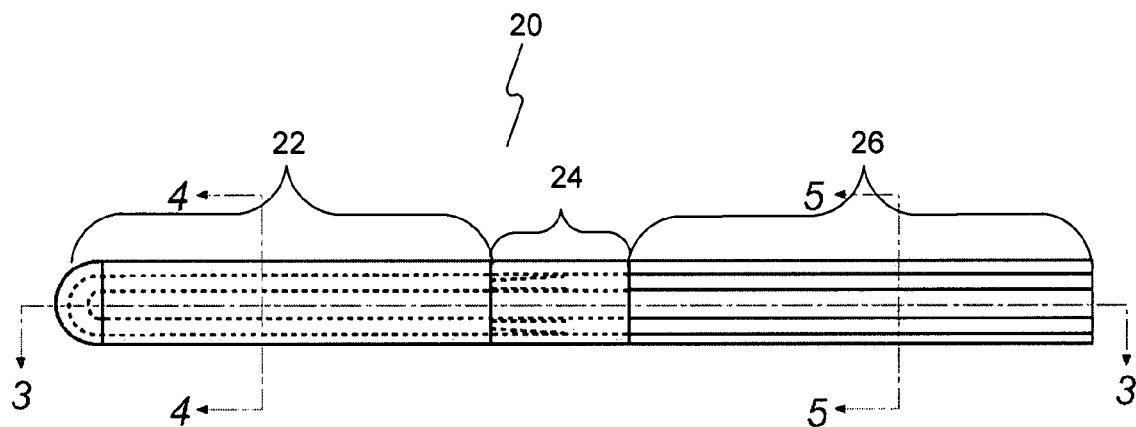
FIG. 2 is a side view of a portion of a guidewire, according to an embodiment of the invention.
Figure 3:
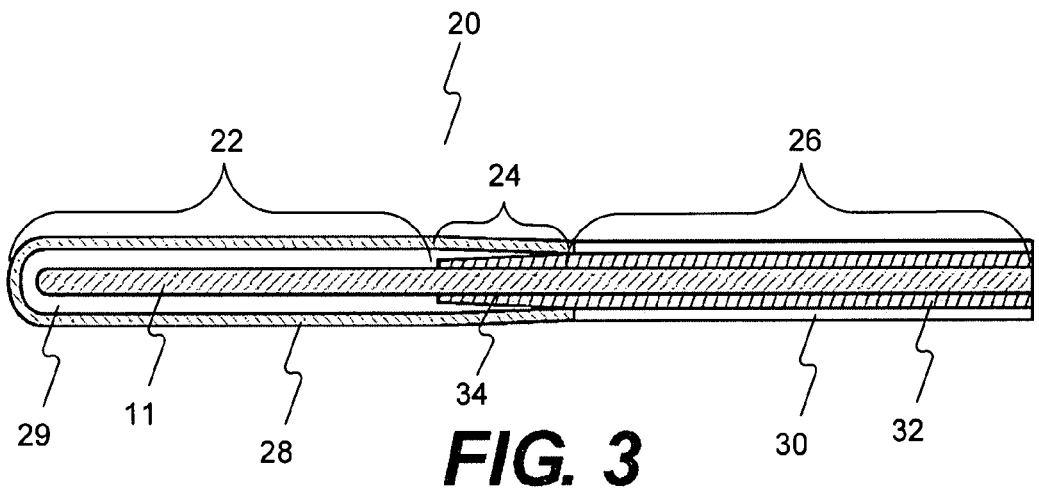
FIG. 3 is a cross-sectional view of the guidewire of FIG. 2 taken along line 3-3 in FIG. 2.

FIG. 2 depicts a side view of a portion of a guidewire 20, according to an embodiment of the invention. FIG. 2 represents an illustration of a distal portion of a guidewire 20. Each of FIGS. 2-5 depict different views of the guidewire 20 after enclosing the underlying core wire assembly 10 and its components in a polymeric covering (e.g., by means of heat shrinking a polyethylene covering). As seen in FIGS. 2 and 3, guidewire 20 includes a distal portion 22, an intermediate portion 24, and a proximal portion 26.

FIG. 3 depicts a cross-sectional view of the guidewire 20 of FIG. 2 taken along line 3-3 in FIG. 2. As seen in FIG. 3, guidewire 20 includes a core wire 11 forming the base of, and extending substantially the entire length of, the guidewire 20. The core wire 11 can be comprised of a various metallic materials, including, but not limited to, stainless steel (including 400 series stainless steel), titanium (including titanium Ti-Beta # alloys), metallic alloys of nickel/titanium (commonly referred to as nitinol), copper, cobalt, vanadium, chromium, iron, and combinations thereof. In one embodiment, core wire 11 can be provided as a rod or other cylindrical shaped metal structure. In addition, the core wire 11 can comprise an unground material having an exterior surface that has not been further machined (e.g., ground in a centerless grinder, milled, or lathed) from the configuration in which it is initially provided. Accordingly, where core wire 11 is an unground material, the profile and cross-section of the core wire 11 remains substantially uniform (i.e. constant) along the length thereof.

FIG. 2 depicts the guidewire 20 after enclosing the underlying core wire assembly 10 in a polymeric covering. For example, guidewire 20 includes a distal portion 22 and an intermediate portion 24 having a polymeric coating 28. Guidewire 20 also includes an additional coating for the remaining proximal portion of the guidewire 20. For example, a proximal polymer coating 30 can cover the proximal portion 26 of the guidewire 20. Exemplary materials for the polymeric coatings 28 and 30 include, but are not limited to, various thermoplastic materials, such as, silicone, vinyl, polyethylene, polypropylene, PTFE, nylon, acrylic, styrene, polycarbonate, and fluoropolymers. In an embodiment, coating 30 is a PTFE heat shrink coating. It is contemplated that either coating 30 or 28 could be provided first during manufacture.

Extrusion is an exemplary process for applying material 32 to wire 11. Extrusion is a manufacturing process by which, for example, a base material is melted and pumped (or otherwise forced) through a preformed die and then cooled into a specific shape that is dependent on the shape of the die. The process of co-extrusion is similar, except that multiple extruders pump more than one material through different portions of a die forming a final product. In addition, operators can extrude a material onto a primary product as an additional overall layer or coating. Alternately, material can be placed in a predetermined defined area of the die, such as, for example, in a stripe or a sequentially alternating material pattern. In the context of thermoplastics for use in medical device applications, many different types of plastics can be extruded into tubing or cylindrical type shapes.

Using a co-extrusion process, depending on among other things the materials used, the resulting products can have very different physical performance characteristics. For example, depending on the materials combined, the resulting product can be soft or hard, clear or opaque, and with varying flexibility along the length thereof. With reference to FIG. 3, reference number 32 represents a co-extruded material of guidewire 20. Co-extruded material 32 can comprise any of a variety of thermoplastic materials selected based on the resulting features of pushability, kink resistance, torqueability, and flexibility (for example, by selection of particular durometer for material 32).

During a manufacturing procedure, an unground wire forming the base for core wire 11 can be extruded through one portion of a die, while material 32 is extruded through another portion of the die (or through a separate die used in combination with a die for the unground wire material). Alternatively, the core wire 11 could be provided as a stock material onto which material 32 is then extruded, without any portion of wire 11 passing through a die. The resulting product of this co-extrusion is a structure where material 32 hardens to form a layer surrounding the underlying unground base core wire 11, thereby forming the core wire assembly 10. As seen in FIG. 3, a distal portion of the material 32 can be tapered to provide stiffness transition leading to a more flexible distal portion of guidewire 20. The taper results in a tapered portion 34 along the material 32. The taper can be formed through a buffing or tipping process, such as those used in conventional catheter forming processes.

It is contemplated that the coating provided along the distal portion 22 and the intermediate portion 24 may also be a co-extruded material. For example, the co-extrusion may include a first material 28 formed of an outer layer of "Black Tecothane" having a certain amount (e.g., approximately 60%) of radiopaque filler material (e.g., tungsten), thereby providing the benefits of a radiopaque material that can be detected via imaging devices. In addition, where co-extruded, the combined coating can be provided with an inner melt liner 29 that exists in a liquid state when heated to a predetermined temperature and then transitions to a solid state upon cooling a certain relative amount. This melt liner (e.g., depicted as item 29 in FIGS. 3-4) fills all the gaps and irregularities of the core wire. Exemplary materials for use as the inner melt liner include, but are not limited to, EVA (Ethyl Vinyl Acetate) or LDPE (Low Density Polyethylene) materials.

The materials for items 28 and 29 may be selected to exhibit a lower durometer than that of the material selected for co-extruded material 32. In this manner, the guidewire characteristics of pushability, kink resistance, torqueability, and flexibility may be controlled such that the distal portion of guide wire exhibits greater flexibility than the proximal portion. For example, the material properties of items 28 and 29 may work in combination with the tapered portion 34 along the material 32 to provide an intermediate stiffness transition zone between a more flexible distal and a more rigid proximal end.

Due to the wide range of materials available for extrusion (and the differing physical characteristics for those materials), in addition to the ability to precisely control stiffness and flexibility via tapering along the guidewire 20, the guidewire 20 can be provided without a wrapped coil along its length. The elimination of a coil further reduces cost and manufacturing time as compared with prior art guidewires. In addition, the elimination of a wrapped coil is of further benefit since current designs featuring stainless steel coil outer layers can cause a guidewire to hang up in tortuous anatomical conditions due to gaps or ledges created along the guidewire from the coil.

Figures 4, 5:
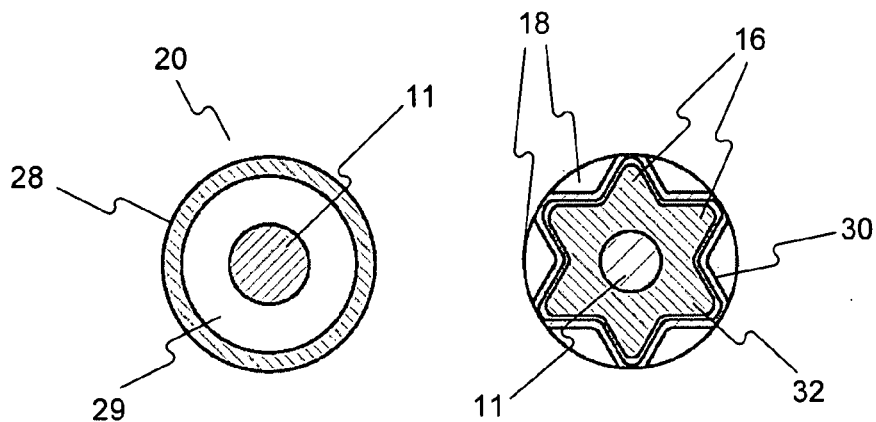
FIG. 4 is a cross-sectional view of the guidewire of FIG. 2 taken along line 4-4 in FIG. 2.
FIG. 5 is a cross-sectional view of the guidewire of FIG. 2 taken along line 5-5 in FIG. 2.

With reference to FIG. 5, another benefit of the co-extrusion formation process for guidewire 20 is the capability to form distinct cross-section profiles for the shape of material 32 surrounding the base wire 11 of core wire assembly 10. For example, FIG. 5 depicts a cross-sectional view of the guidewire 20 of FIG. 2 taken along line 5-5 in FIG. 2. As one example, the cross-sectional shape of co-extruded material 32 is a star shaped pattern forming a predetermined number of fins 16 alternating between troughs 18 along an exterior perimeter of material 32. A wide range of shapes (e.g., including, but not limited to, rectangular, triangular, or any other polygon cross-sectional shape) could be provided along the exterior perimeter of material 32 depending on the predetermined shape of the extrusion die.

As seen in FIG. 5, the exterior perimeter of material 32 (forming a star shape in the illustrated example) can be covered with a snug lubricous friction reducing polymer coating 30, such as, for example, a heat shrink PTFE (polyyetrafluoroethylene) coating. In the distally directed cross-sectional view of FIG. 5, the distally spaced circular shape of polymeric coating 28 is visible with the core wire 11, material 32, and polymer coating 28 shown in cross-hatched lines depicting a cross-section. As an alternative to the illustrated star cross-section pattern, guidewire profiles could be manufactured to dictate the bend direction of the guidewire. For example, sections or grooves could be cut into the plastic portion of the core wire for this purpose. Such grooves or sections could be provided along particular portions of the guidewire such that a resulting guidewire cross section exhibits a particular desired moment of inertia relative to other portions of the guidewire in order to control bending or flexibility in one direction or another.

The illustrated star pattern for material 32 (and its polymeric covering 30) is advantageous in that it provides a profile along a portion of the guide wire having a reduced area along the guidewire perimeter that is susceptible to contact with an internal surface of a working channel in an endoscope. In other words, due to the troughs 18 along an exterior perimeter of material 32, less area is capable of contact within an internal surface of a working channel in an endoscope. Accordingly, the configuration results in reduced friction during movement of the guidewire 20 within a endoscope working channel. In addition, the material displaced by the formation of the troughs 18 along an exterior perimeter of guidewire 20 allows more area for fluid flow or additional treatment instruments within a working channel.

Figure 6:
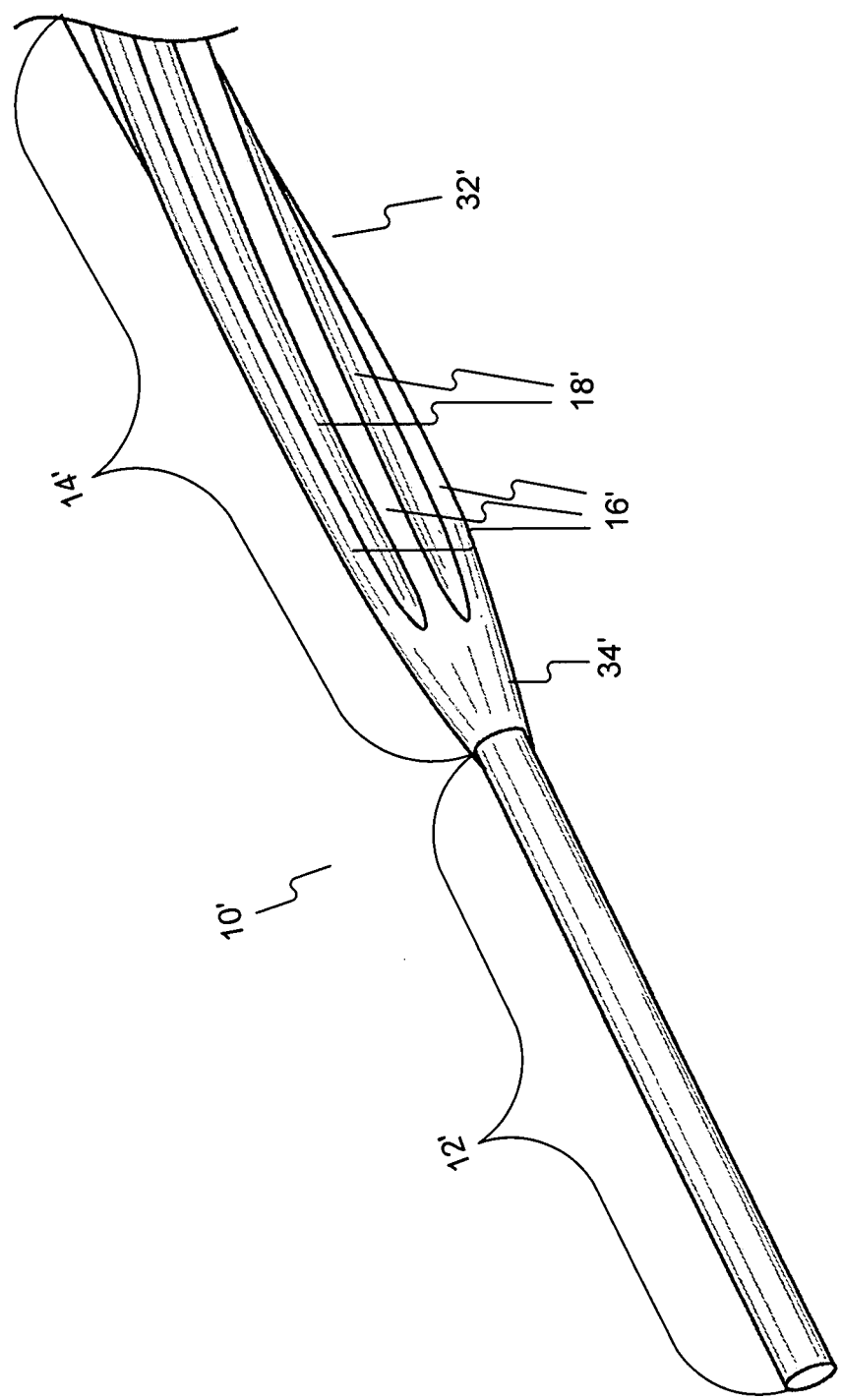
FIG. 6 is a perspective view of an extruded core for a guidewire, according to another embodiment of the invention.

FIG. 6 depicts a perspective view of a core wire assembly 10' for use with a guidewire. Core wire assembly 10' illustrates further options for controlling flexibility and other guidewire performance characteristics. FIG. 6 depicts a core wire assembly 10' having a distal portion 12' and a proximal portion 14'. An underlying core wire 11' is provided as a base component of the core wire assembly 10'. Similar to the arrangement of FIG. 1, core wire assembly 10' includes a co-extruded material 32' formed along a proximal portion of the core wire assembly 10'. The co-extruded material 32' forms an exterior configuration having a plurality of fins 16' alternately arranged between a plurality of troughs 18'. The material 32' can form a star shaped pattern along the exterior surface of proximal portion 14'. In the embodiment of FIG. 6, the fins 16' and troughs 18' are provided in a twisted configuration to exhibit a spiral star shaped pattern. The spiral star pattern of FIG. 6 could be twisted to at any given pitch in order to provide any predetermined flexibility to the core wire assembly 10'.

Referring to FIG. 7, there is depicted a side view a portion of a guidewire 50, according to another embodiment of the invention. As seen in FIG. 7 and the FIG. 8 cross-section, the guidewire 50 includes an unground core wire 52, a distal portion 54, and a proximal portion 56. In the embodiment of FIGS. 7-8, instead of including a co-extruded material 32 as in FIGS. 3-4, an unground core wire 52 is wrapped or cabled with wound wire along the proximal portion 56 of guidewire 50. Just as in the embodiments described above, the core wire 52 of guidewire 50 can be unground, extend substantially the entire length of the guidewire 50, and be comprised of a various metallic materials, including, but not limited to, stainless steel (including 400 series stainless steel), titanium (including titanium Ti-Beta # alloys), metallic alloys of nickel/titanium (commonly referred to as nitinol), copper, cobalt, vanadium, chromium, iron, and combinations thereof.

An inner polymer layer 61 (such as, e.g., PTFE or Polyimide) is provided over the core wire 52. Then a proximal portion of core wire 52 and the inner polymer layer 61 are wrapped with a wire 58. An additional, outer polymer layer 64 is then provided over wrapped wire 58, thereby sandwiching the wire 58 between the inner 61 and outer 64 polymer layers. For purposes of explanation, a portion of the outer polymer layer 64 is omitted from the proximal end of the guide wire 50, thereby depicting an exposed portion of the wrapped wire 58. It should be understood that the outer layer 64 may extend proximally to the terminal proximal end of guide wire 50. The proximal portion of the core wire 52, wrapped with wire 58, controls the performance characteristics of pushability, kink resistance, torqueability, and flexibility. The wire 58 terminates a certain distance before the distal end of the inner polymer layer 61, thereby exposing a length 63 of the inner polymer layer 61 beyond the wire 58. This configuration provides more of an intermediate transition between a more stiff proximal arrangement to a more flexible arrangement at the distal end. Exemplary materials for the inner 61 and outer 64 polymers include, but are not limited to, various thermoplastic materials, such as, silicone, vinyl, polyethylene, polypropylene, nylon, acrylic, styrene, polycarbonate, and fluoropolymers.

Just as described above for an alternate arrangement at a distal portion of the device of FIG. 3, it is also contemplated that a coating provided along the distal portion 54 may be a co-extruded material. For example, the co-extrusion for may include a first, outer layer 62 of "Black Tecothane" having a certain amount (e.g., approximately 60%) of a radiopaque filler material (e.g., tungsten), thereby providing the benefits of a radiopaque material detectable via imaging devices. In addition, where co-extruded, the first layer 62 can be combined with an inner melt liner 60 covering a distal portion of wire 58, the exposed length 63 of the inner polymer layer 61, and the distal portion of the core wire 52. In other words, the melt liner 60 is provided between the outer layer 62 and the core wire 52 along a distal portion of the guide wire 50. The melt liner material 60 exists in a liquid state when heated to a predetermined temperature and then transitions to a solid state upon cooling down a certain relative amount. This melt liner 60 fills all the gaps and irregularities of the core wire. Exemplary materials for use as the inner melt liner include, but are not limited to, EVA (Ethyl Vinyl Acetate) or LDPE (Low Density Polyethylene) materials.

Just as described above regarding FIGS. 3-4, the materials for items 62 and 60 may be selected to provide greater flexibility at the distal end of the guide wire. In this manner, the guidewire characteristics of pushability, kink resistance, torqueability, and flexibility may be controlled such that the distal portion of guide wire exhibits greater flexibility than the proximal portion.

In the arrangement of FIGS. 7-8, there is a transition zone in the region where the exterior surface of the guide wire 50 transitions between that of the outer layer 62 and that of the outer polymer layer 64. In one embodiment, a portion of the outer polymer layer 64 may be removed from a distal portion of the wrapped wire 58. This reduced diameter distal portion of the wrapped wire 58 is then coated with a proximal portion of the co-extruded material (i.e., the co-extruded material comprised of outer layer 61 and the inner melt liner 60) described above. The co-extruded material may provide an outer diameter substantially equal to that of the outer polymer layer 64 such that the guide wire exhibits a relatively constant outer diameter.

FIG. 8 is a cross-sectional view of the guidewire of FIG. 7 taken along line 8-8 in FIG. 7. For purposes of clarity, however, the wound wire 58 is not depicted in cross-section. As seen in FIG. 8, the wrapping of wire 58 over the inner polymer layer 61 and around the proximal portion of core wire 52 can be customized to produce any variety of flexibility and/or stiffness along guidewire 50. At the distal portion of the guidewire 50 where the wire 58 terminates, melt liner 60 and outer layer 62 provide a stiffness transition element along a distal portion of the guidewire to shift to a more flexible distal end from a more stiff proximal end. In the embodiment of FIGS. 7-8, the wrapped wire 58 can be provided over an unground core 52. Accordingly, the use of the wrapped wire is advantageous in that the wrapping can be customized in order to provide a wide range of performance characteristics to the guidewire, without requiring the costly procedure of machining a core with a center-less grinder.

Other embodiments of the invention will be apparent to those skilled in the art from consideration of the specification and practice of the invention disclosed herein. It is to be understood that the guidewires of the present disclosure are not intended for any particular medical procedure. As non limiting examples, it is contemplated that the devices disclosed in this application could be used for access of a patient's vascular system, urological applications, digestive system applications, as well as respiratory system applications. It is intended that the specification and examples be considered as exemplary only, with a true scope and spirit of the invention being indicated by the following claims.

What is claimed is:

1. A guidewire comprising:
   an elongate core wire, the core wire being unground, having a length from a proximal end to a distal end thereof substantially corresponding to a length from a proximal end to a distal end of the guidewire, and having a substantially uniform cross-sectional area along the length thereof; and
   a thermoplastic material extruded along the core wire and surrounding a portion of the core wire,
   wherein the thermoplastic material covers only a proximal portion of the core wire and includes a tapered portion,
   wherein a portion of the core wire not covered with the thermoplastic material is covered with a polymer, the polymer extending from a distal end of the guidewire and terminating along the tapered portion of the thermoplastic material,
   wherein the polymer comprises an outer layer and an inner layer, and
   wherein the inner layer has a thickness decreasing from a distal end of the tapered portion to a proximal end of the tapered portion and the outer layer has a thickness remaining constant from the distal end of the tapered portion to the proximal end of the tapered portion.

2. The guidewire of claim 1, wherein the outer layer includes a radiopaque filler material.

3. The guidewire of claim 1, wherein the inner layer comprises an EVA (Ethyl Vynyl Acetate) material or a LDPE (Low Density Polyethylene) material.

4. A guidewire comprising:
   an elongate core wire, the core wire being unground, having a length from a proximal end to a distal end thereof substantially corresponding to a length from a proximal end to a distal end of the guidewire, and having a substantially uniform cross-sectional area along the length thereof; and
   a thermoplastic material extruded along the core wire and surrounding a portion of the core wire, the thermoplastic material having a tapered portion,
   wherein a portion of the core wire not covered with the thermoplastic material is covered with a polymer, the polymer extending from a distal end of the guidewire and terminating along the tapered portion of the thermoplastic material,
   wherein the polymer comprises an inner layer having a thickness decreasing from a distal end of the tapered portion to a proximal end of the tapered portion and an outer layer having a thickness remaining constant from the distal end of the tapered portion to the proximal end of the tapered portion, and
   wherein the thermoplastic material exhibits a substantially star shaped cross-section.

5. A guidewire comprising:
   an elongate core wire, the core wire being unground, having a length from a proximal end to a distal end thereof substantially corresponding to a length from a proximal end to a distal end of the guidewire, and having a substantially uniform cross-sectional area along the length thereof; and
   a thermoplastic material extruded along the core wire and surrounding a portion of the core wire, the thermoplastic material having a tapered portion,
   wherein a portion of the core wire not covered with the thermoplastic material is covered with a polymer, the polymer extending from a distal end of the guidewire and terminating along the tapered portion of the thermoplastic material,
   wherein the polymer comprises an inner layer having a thickness decreasing from a distal end of the tapered portion to a proximal end of the tapered portion and an outer layer having a thickness remaining constant from the distal end of the tapered portion to the proximal end of the tapered portion, and
   wherein an exterior surface of the thermoplastic material comprises a plurality of fins.

6. The guidewire of claim 5, wherein each of the plurality of fins is separated along the exterior surface of the thermoplastic material by one of a plurality of troughs.

7. A guidewire comprising:
   an elongate core wire, the core wire being unground, having a length from a proximal end to a distal end thereof substantially corresponding to a length from a proximal end to a distal end of the guidewire, and having a substantially uniform cross-sectional area along the length thereof; and
   a thermoplastic material extruded along the core wire and surrounding a portion of the core wire,
   wherein a distal portion of the thermoplastic material is tapered to have a smaller cross-section than a remaining proximal portion of the thermoplastic material,
   wherein a portion of the core wire not covered with the thermoplastic material is covered with a polymer, the polymer extending from a distal end of the guidewire and terminating along the distal portion of the thermoplastic material,
   wherein the polymer comprises an inner layer having a thickness decreasing from a distal end of the distal portion to a proximal end of the distal portion and an outer layer having a thickness remaining constant from the distal end of the distal portion to the proximal end of the distal portion,
   wherein a non-tapered portion of the thermoplastic material has an exterior surface comprising a plurality of fins.

8. The guidewire of claim 7, wherein each of the plurality of fins is separated along the exterior surface of the thermoplastic material by one of a plurality of troughs.

9. A guidewire comprising:
an elongate core wire, the core wire being unground, having a length from a proximal end to a distal end thereof substantially corresponding to a length from a proximal end to a distal end of the guidewire, and having a substantially uniform cross-sectional area along the length thereof; and
a thermoplastic material extruded along the core wire and surrounding only a portion of the core wire, the thermoplastic material having a tapered portion,
wherein the thermoplastic material covers a proximal portion of the core wire,
wherein the proximal portion of the core wire is further covered with a first polymer,
wherein a portion of the core wire not covered with the thermoplastic material is covered with a second polymer different than the first polymer, the second polymer extending from a distal end of the guidewire and terminating along the tapered portion of the thermoplastic material, and
wherein the second polymer comprises an inner layer having a thickness decreasing from a distal end of the tapered portion to a proximal end of the tapered portion and an outer layer having a thickness remaining constant from the distal end of the tapered portion to the proximal end of the tapered portion.

10. The guidewire of claim 9, wherein the inner layer comprises an EVA (Ethyl Vynyl Acetate) material or a LDPE (Low Density Polyethylene) material.

11. A guidewire comprising:
an elongate core wire, the core wire being unground, having a length from a proximal end to a distal end thereof substantially corresponding to a length from a proximal end to a distal end of the guidewire, and having a substantially uniform cross-sectional area along the length thereof; and
a thermoplastic material extruded along the core wire and surrounding a portion of the core wire, the thermoplastic material having a tapered portion, wherein a portion of the core wire not covered with the thermoplastic material is covered with a polymer, the polymer extending from a distal end of the guidewire and terminating along the tapered portion of the thermoplastic material,
wherein the polymer comprises an inner layer having a thickness decreasing from a distal end of the tapered portion of the thermoplastic material to a proximal end of the tapered portion of the thermoplastic material and an outer layer having a thickness remaining constant from the distal end of the tapered portion to the proximal end of the tapered portion.

12. The guidewire of claim 11, wherein the thermoplastic material exhibits a substantially star shaped cross-section.

13. The guidewire of claim 11, wherein the thermoplastic material has a plurality of longitudinally extending and circumferentially spaced troughs.

14. The guidewire of claim 11, wherein the thermoplastic material covers a proximal portion of the core wire.

15. The guidewire of claim 11, wherein the inner layer comprises an EVA (Ethyl Vynyl Acetate) material or a LDPE (Low Density Polyethylene) material.

16. The guidewire of claim 11, wherein the thermoplastic material comprises silicone, vinyl, polyethylene, polypropylene, nylon, acrylic, styrene, polycarbonate, polyether block amide, fluoropolymer, or combinations thereof.

* * * * *